(12) United States Patent
Ishikawa et al.

(10) Patent No.: US 11,286,272 B2
(45) Date of Patent: *Mar. 29, 2022

(54) PRODUCTION METHOD FOR ACIDIC XYLOOLIGOSACCHARIDE, AND ACIDIC XYLOOLIGOSACCHARIDE

(71) Applicant: OJI HOLDINGS CORPORATION, Tokyo (JP)

(72) Inventors: Kotaro Ishikawa, Tokyo (JP); Takuro Kashiwamura, Tokyo (JP); Takuya Kato, Tokyo (JP); Toru Koga, Tokyo (JP); Suguru Ishikawa, Tokyo (JP)

(73) Assignee: OJI HOLDINGS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/643,215

(22) PCT Filed: Aug. 31, 2017

(86) PCT No.: PCT/JP2017/031433
§ 371 (c)(1),
(2) Date: Feb. 28, 2020

(87) PCT Pub. No.: WO2018/043667
PCT Pub. Date: Mar. 8, 2018

(65) Prior Publication Data
US 2020/0207796 A1 Jul. 2, 2020

(30) Foreign Application Priority Data
Aug. 31, 2016 (JP) ................... 2016-169709

(51) Int. Cl.
*C07H 3/06* (2006.01)
*C07H 1/08* (2006.01)
*C13K 13/00* (2006.01)

(52) U.S. Cl.
CPC ................ *C07H 3/06* (2013.01); *C07H 1/08* (2013.01); *C13K 13/007* (2013.01)

(58) Field of Classification Search
None
See application file for complete search history.

(56) References Cited

U.S. PATENT DOCUMENTS

| | | | |
|---|---|---|---|
| 4,168,742 A | 9/1979 | Kluppel et al. | |
| 4,699,900 A | 10/1987 | Bayol et al. | |
| 4,713,373 A | 12/1987 | Bayol et al. | |
| 4,727,063 A | 2/1988 | Naggi et al. | |
| 5,516,765 A | 5/1996 | Andermann | |
| 7,902,158 B2 | 3/2011 | Kuszmann et al. | |
| 8,987,216 B2 | 3/2015 | Kuszmann et al. | |
| 8,993,536 B2 | 3/2015 | Kakehi et al. | |
| 2001/0005720 A1 | 6/2001 | Striker et al. | |
| 2003/0109491 A1 | 6/2003 | Ulmer et al. | |
| 2006/0194759 A1 | 8/2006 | Eidelson | |
| 2007/0281893 A1 | 12/2007 | Kuszmann et al. | |
| 2008/0249298 A1 | 10/2008 | Ulmer et al. | |
| 2010/0055060 A1 | 3/2010 | Yoshida et al. | |
| 2010/0261807 A1 | 10/2010 | Laine et al. | |
| 2011/0118198 A1 | 5/2011 | Kuszmann et al. | |
| 2011/0251154 A1 | 10/2011 | Stajic et al. | |
| 2011/0281819 A1 | 11/2011 | Kakehi et al. | |
| 2011/0306567 A1 | 12/2011 | Schofield et al. | |
| 2020/0062867 A1 | 2/2020 | Ishikawa et al. | |

FOREIGN PATENT DOCUMENTS

| | | |
|---|---|---|
| CA | 2018133 A1 | 12/1990 |
| CN | 1051564 A | 5/1991 |
| CN | 1832966 A | 9/2006 |
| CN | 101014607 A | 8/2007 |
| CN | 102061323 A | 5/2011 |
| CN | 102300870 A | 12/2011 |
| CN | 102766225 A | 11/2012 |
| CN | 103320548 A | 9/2013 |
| CN | 105907896 A | 8/2016 |
| CN | 106832020 A | 6/2017 |
| EP | 0 116 801 B1 | 4/1987 |
| EP | 0889055 A1 | 7/1999 |
| JP | S48-043100 B1 | 12/1973 |
| JP | S60-063203 A | 4/1985 |
| JP | S61-130301 A | 6/1986 |

(Continued)

OTHER PUBLICATIONS

Office Action dated Nov. 16, 2020 in Australian Application No. 2018276567.
Extended European Search Report dated Feb. 3, 2021, from the European Patent Office in EP application No. 18809395.9, corresponding to U.S. Appl. No. 16/617,783.
"Technology of Wood Chemicals", CMC Publishing Co., Ltd., 2007, p. 108.
Koshijima, "Recent Problems of Hemicellulose Chemistry", Material, 1967, vol. 16, pp. 758-764.
International Preliminary Report on Patentability for PCT/JP2018/007138 dated Oct. 24, 2018 corresponding to U.S. Appl. No. 16/489,074.
International Search Report for PCT/JP2018/007138 dated Mar. 27, 2018 corresponding to U.S. Appl. No. 16/489,074.
Ishihara et al., "Isolation of Xylan from Hardwood by Alkali Extraction and Steam Treatment", Mokuzai Gakkaishi, Journal of Wood Science 1996, vol. 42, No. 12, pp. 1211-1220 (11 pages total).
Kabel et al., "Hydrothemially treated xylan rich by-products yield different classes of xylo-oligosaccharides" Carbohydrate Polymers, 2002, vol. 50, No. 1, pp. 47-56.

(Continued)

Primary Examiner — Dale R Miller
(74) Attorney, Agent, or Firm — Sughrue Mion, PLLC

(57) ABSTRACT

The present invention provides a reduced-cost method for producing an acidic xylooligosaccharide, the method including a depolymerization step of depolymerizing a plant-derived raw material and a deacetylation step of adding a base to a solution of the product of the depolymerization step to achieve a pH of 11 or higher. The present invention further provides an acidic xylooligosaccharide having an acetyl group content of 0 to 5.0 mass %. The acidic xylooligosaccharide of the present invention, which has an acetyl group content of 0 to 5.0 mass %, can be used as a starting material in a production method to thereby obtain pentosan polysulfate with a high yield.

7 Claims, 2 Drawing Sheets

(56) References Cited

FOREIGN PATENT DOCUMENTS

| | | |
|---|---|---|
| JP | S61-130302 A | 6/1986 |
| JP | S61-197601 A | 9/1986 |
| JP | S62-004362 B2 | 1/1987 |
| JP | H03-20225 A | 1/1991 |
| JP | H09-509650 A | 9/1997 |
| JP | H10-195107 A | 7/1998 |
| JP | H11-049802 A | 2/1999 |
| JP | H11-180821 A | 7/1999 |
| JP | 2003-183303 A | 7/2003 |
| JP | 2003-221307 A | 8/2003 |
| JP | 2003-221339 A | 8/2003 |
| JP | 2004-513185 A | 4/2004 |
| JP | 2005-501931 A | 1/2005 |
| JP | 2009-196915 A | 9/2009 |
| JP | 2009-532467 A | 9/2009 |
| JP | 2013-177433 A | 9/2013 |
| JP | 2014-129383 A | 7/2014 |
| JP | 2015-038061 A | 2/2015 |
| JP | 2016-514090 A | 5/2016 |
| JP | 6225321 B1 | 11/2017 |
| JP | 6281659 B1 | 2/2018 |
| WO | 1991/016058 A1 | 10/1991 |
| WO | 1995/014491 A3 | 6/1995 |
| WO | 1995/014492 A2 | 6/1995 |
| WO | 1998/006409 A2 | 2/1998 |
| WO | 02/041901 A1 | 5/2002 |
| WO | 2005/014656 A1 | 2/2005 |
| WO | 2005/117912 A1 | 12/2005 |
| WO | 2007/014155 A2 | 2/2007 |
| WO | 2007/123800 | 11/2007 |
| WO | 2007/138263 A1 | 12/2007 |
| WO | 2008/107906 A1 | 9/2008 |
| WO | 2009/087581 A1 | 7/2009 |
| WO | 2010/000013 A1 | 1/2010 |
| WO | 2010/089617 A2 | 8/2010 |
| WO | 2010/089617 A3 | 8/2010 |
| WO | 2012/101544 A1 | 8/2012 |
| WO | 2012/114349 A1 | 8/2012 |
| WO | 2013/186857 A1 | 12/2013 |
| WO | 2014/114723 A1 | 7/2014 |
| WO | 2014/122251 A2 | 8/2014 |
| WO | 2014/122251 A3 | 8/2014 |
| WO | 2016/184887 A1 | 11/2016 |
| WO | WO-2016184887 A1 * 11/2016 ......... C08B 37/0057 |
| WO | 2016/191698 A1 | 12/2016 |
| WO | 2018/043667 A1 | 3/2018 |
| WO | 2018/043668 A1 | 3/2018 |

OTHER PUBLICATIONS

Kabel et al., "Complex xylo-oligosaccharides identified from hydrothermally treated Eucalyptus wood and brewery's spent grain", Carbohydrate Polymers, 2002, vol. 50, No. 2, pp. 191-200.
Koutaniemi et al., "Distinct roles of carbohydrate esterase family CE16 acetyl esterases and polymer-acting acetyl xylan esterases in xylan deacetylation", Journal of Biotechnology, 2013, vol. 168, No. 4, pp. 684-692.
Pawar et al., "Acetylation of woody lignocellulose: significance and regulation", Frontiers in Plant Science, 2013, vol. 4, No. 118, pp. 1-8.
International Search Report for PCT/JP2017/031434 dated Oct. 31, 2017 corresponding to U.S. Appl. No. 16/643,265.
Office Action issued by the Japanese Patent Office dated Apr. 18, 2017 in JP Application No. 2017-040067.
Office Action issued by the Japanese Patent Office dated Oct. 3, 2017 in JP Application No. 2017-166559.
Moure et al., "Advances in the manufacture, purification and applications of xylo-oligosaccharides as food additives and nutraceuticals", Process Biochemistry, 2006, vol. 41, Issue 9, pp. 1913-1923.
Gullón et al., "Structural features and properties of soluble products derived from Eucalyptus globulus hemicelluloses", Food Chemistry, 2011, vol. 127, No. 4, p. 1798-1807.
Gullón et al., "Membrane processing of liquors from Eucalyptus globulus autohydrolysis", Journal of Food Engineering, 2008, vol. 87, No. 2, pp. 257-265.
Ishikawa et al., "Research and development of sulphated hemicellulose (PPS)", The 62nd Japan Technical Association of the Pulp and Paper Industry Annual Meeting, 2019, pp. 1-5.
Scully et al., "The antiheparin effect of a heparinoid, pentosane polysulphate", Biochem. J, 1984, vol. 218, pp. 657-665.
Mccarty et al., "Sulfated glycosaminoglycans and glucosamine may synergize in promoting synovial hyaluronic acid synthesis", Medical Hypotheses, 2000, vol. 54, No. 5, pp. 798-802.
Ferrao et al., "The effect of heparin on cell proliferation and type-1 collagen synthesis by adult human dermal fibroblasts", Biochimica et Biophysica Acta, 1993, vol. 1180, pp. 225-230.
International Search Report for PCT/JP2018/020644 dated Sep. 4, 2018, corresponding to U.S. Appl. No. 16/617,783.
International Search Report for PCT/JP2017/031433 dated Oct. 31, 2017 corresponding to the present application.
Office Action issued by the Japanese Patent Office dated Jan. 8, 2019 in JP Application No. 2018-553269.
Office Action issued by the Japanese Patent Office dated Feb. 5, 2019 in JP Application No. 2018-229611.
Hirst et al., "Water-soluble Polysaccharides of Cladophora" Journal of the Chemical Society, 1965, pp. 2958-2967.
International Search Report for PCT/JP2018/033535 dated Nov. 27, 2018, corresponding to U.S. Appl. No. 16/646,243.
International Search Report for PCT/JP2018/046537 dated Mar. 5, 2019.
International Search Report for PCT/JP2017/031432 dated Oct. 31, 2017.
Office Action issued by the Japanese Patent Office dated Jul. 17, 2019 in JP Application No. 2018-516078.
Office Action issued by the Japanese Patent Office dated Jul. 17, 2019 in JP Application No. 2018-516079.
González et al., "Demonstration of Inhibitory Effect of Oral Shark Cartilage on Basic Fibroblast Growth Factor-Induced Angiogenesis in the Rabbit Cornea", Biol. Pharm. Bull, 2001, vol. 24, No. 2, pp. 151-154.
Swain et al., "Heparin-Binding Growth Factor Blockade with Pentosan Polysulfate", Annals of the New York Academy of Sciences, 1993, vol. 698, pp. 63-70.
Zugmaier et al., "Polysulfated Heparinoids Selectively Inactivate Heparin-Binding Angiogenesis Factors", Annals of the New York Academy of Sciences, 1999, vol. 886, pp. 243-248.
Zugmaier et al., "Inhibition by Pentosan Polysulfate (PPS) of Heparin-Binding Growth Factors Released From Tumor Cells and Blockage by PPS of Tumor Growth in Animals", Journal of the National Cancer Institute, 1992, vol. 84, No. 22, pp. 1716-1724.
Garrote et al., "Non-isothermal autohydroiysis of Eucalyptus wood", Wood Science and Technology, 2002, vol. 36, pp. 111-123.
Sivová et al., "Fagus sylvatica glucuronoxylan sulfate-chemical profile and pharmacological view", Starch, 2015, vol. 68, pp. 621-628.
Rhee et al., "Engineering the Xylan Utilization System in Bacillus subtilis for Production of Acidic Xylooligosaccharides", Applied and Environmental Microbiology, 2014, vol. 80, No. 3, pp. 917-927.
Maekawa et al., "Infrared Spectra of Wood Cellulose and Related Polysaccharide", Kyoto University, Research Institute Report, 1968, vol. 43, pp. 1-8.
Kabel et al., "In Vitro Fermentability of Differently Substituted Xylo-oligosaccharides", Journal of Agricultural and Food Chemistry, 2002, vol. 50, pp. 6205-6210.
Office Action issued by Japanese Patent Office dated Oct. 9, 2018 in JP Application No. 2018-516078.
International Preliminary Report on Patentability dated Dec. 3, 2019 from the International Bureau in International Application No. PCT/JP2018/020644, corresponding to U.S. Appl. No. 16/617,783.
U.S. Appl. No. 16/617,783, filed Nov. 27, 2019, Kotaro Ishikawa et al.
U.S. Appl. No. 16/489,074, filed Aug. 27, 2019, Kotaro Ishikawa et al.
U.S. Appl. No. 16/643,265, filed Feb. 28, 2020, Kotaro Ishikawa et al.

(56) References Cited

OTHER PUBLICATIONS

U.S. Appl. No. 16/646,243, filed Mar. 11, 2020, Kotaro Ishikawa et al.
Stephen Dealler et al., "Pentosan polysulfate as a prophylactic and therapeutic agent against prion disease", IDrugs, vol. 6, No. 5, Jun. 1, 2003, pp. 470-478, XP055777416 (10 pages total).
Extended European Search Report dated Feb. 26, 2021 from the European Patent Office in EP Application No. 16/643,265, corresponding to U.S. Appl. No. 16/643,265.
ELMIRON®—100 Mg (Pentosan Polysulfate Sodium)Capsules, 2002, https://www.accessdata.fda.gov/drugsatfda_docs/label/2020/020193s014lbl.pdf (14 pages).
Office Action dated Mar. 25, 2021 issued by the Indian Patent Office in Indian Application No. 201947036653.
Office Action dated Apr. 27, 2021 in U.S. Appl. No. 16/646,243.
Office Action dated Mar. 2, 2021 in U.S. Appl. No. 16/489,074.
Stephan Daus et al., "Homogeneous Sulfation of Xylan from Different Sources", Macromolecular Materials and Engineering, 2011, vol. 296, pp. 551-561 (11 pages).
Teleman et al., "Characterization of O-acetyl-(4-O-methylglucurono)xylan isolated from birch and beech", Carbohydrate Research, 2002, vol. 337, pp. 373-377 (5 pages total).
Office Action dated Sep. 17, 2021 by Indian Patent Office in Indian Application No. 202047012044.
Office Action dated Aug. 30, 2021 by China National Intellectual Property Administration in Chinese Application No. 201780094371.2.
Mi et al., "Preparation of corn stover pentosan sulfate", Journal of Changchun University of Technology (Natural Science Edition), 2014, vol. 35, No. 6, pp. 716-719 (4 pages total).
Extended European Search Report dated Sep. 29, 2021 by European Patent Office in European Application No. 18890627.5.
Herbert et al., "Activity of Pentosan Polysulphate and Derived Compounds on Vascular Endothelial Cell Proliferation and Migration Induced by Acidic and Basic FGF In Vitro", Biochemical Pharmacology, 1988, vol. 37, No. 22, pp. 4281-4288 (8 pages total).
Office Action dated Oct. 26, 2021 in U.S. Appl. No. 16/955,641.
Gura, "Cancer Models: Systems for Identifying New Drugs Are Often Faulty", Science, 1997, vol. 278, No. 5340, pp. 1041-1042 (6 pages total).
"The Merck Manual", Sixteenth Edition, 1992, pp. 339-342 and 1488-1490 (6 pages total).
Smith et al., "Cancer, inflammation and the ATI and AT2 receptors", Journal of Inflammation, 2004, vol. 1, No. 3, pp. 1-12 (12 pages total).
Vergnolle et al., "Protease-activated receptors and inflammatory hyperalgesia", Mem Inst Oswaldo Cruz, Rio de Janeiro, 2005, vol. 100 (Suppl. I), pp. 173-176 (4 pages total).
Douglass et al., "1. Diagnosis, treatment and prevention of allergic disease: the basics", MJA Practice Essentials—Allergy, 2006, vol. 185, No. 4, pp. 228-233 (6 pages total).
Office Action dated Oct. 25, 2021 issued by China National Intellectual Property Administration in Chinese Patent Application No. 201880058953.X, which corresponds to U.S. Appl. No. 16/646,243.
Communication dated Jan. 4, 2022 from the Indian Patent Office in Indian Application No. 202047029636, corresponding to U.S. Appl. No. 16/955,641.

\* cited by examiner

PRODUCTION METHOD FOR ACIDIC XYLOOLIGOSACCHARIDE, AND ACIDIC XYLOOLIGOSACCHARIDE

CROSS REFERENCE TO RELATED APPLICATIONS

This application is a National Stage of International Application No. PCT/JP2017/031433 filed Aug. 31, 2017.

TECHNICAL FIELD

The present invention relates to a method for producing an acidic xylooligosaccharide, and an acidic xylooligosaccharide. Specifically, the present invention relates to an acidic xylooligosaccharide having a low acetyl group content, and a method for producing the acidic xylooligosaccharide.

BACKGROUND ART

Acidic sugars have heretofore been used for functional foods, pharmaceuticals, or intermediates of active pharmaceutical ingredients. Acidic sugars include those that exhibit various physiological activities, such as improving blood properties and activating lipid metabolism. For example, pectin is known as a dietary fiber-containing acidic sugar. Pectin has been studied for its use as a pharmaceutical agent for ameliorating hyperlipidemia or suppressing an increase in blood insulin, in addition to its application to functional foods.

Acidic xylooligosaccharide is also one of the acidic sugars expected to be applicable as an intermediate for an active pharmaceutical ingredient. Acidic xylooligosaccharides are xylooligosaccharides having at least one uronic acid residue as a side chain in a xylooligosaccharide molecule (Patent Literature (PTL) 1).

Xylooligosaccharide is a sugar that has physiological activities of both oligosaccharide and dietary fiber. In particular, xylooligosaccharides that have an average degree of polymerization of around 12 are known to exhibit a dietary fiber-like intestinal function-regulating action. Xylooligosaccharide is usually a neutral sugar that becomes less soluble with an increase of its chain length. However, the degree of solubility of xylooligosaccharide can be increased by introducing an acid residue as a side chain to form an acidic xylooligosaccharide. Such an acidic xylooligosaccharide is expected to be applicable not only as a functional food, but also as a material that can be used for cosmetics, pharmaceuticals, and the like (for example, Patent Literature (PTL) 2 and Patent Literature (PTL) 3).

Patent Literature (PTL) 1 discloses an acidic xylooligosaccharide composition containing an acidic xylooligosaccharide having at least one uronic acid residue as a side chain in a xylooligosaccharide molecule, and having an average degree of polymerization of 8 to 15. In PTL 1, a lignocellulose material is enzymatically treated to obtain a complex of a xylooligosaccharide component and a lignin component; and the complex is then acidically hydrolyzed to obtain a xylooligosaccharide mixture, from which an acidic xylooligosaccharide mixture is separated, to thereby obtain an acidic xylooligosaccharide. In PTL 1, a lignocellulose material is enzymatically treated with a neutral thermophilic xylanase derived from the genus *Bacillus* to thereby produce an acidic xylooligosaccharide having a relatively high average degree of polymerization.

Xylans of hardwoods are known to have 5 to 7 acetyl groups per 10 xyloses at 2-position or 3-position under natural conditions (Non-patent Literature (NPL) 1). Patent Literature (PTL) 4 discloses that xylan, which is used as a starting material for producing an acidic xylooligosaccharide, contains a xylose unit that binds to uronic acid at 4-position, and that is acetylated at 3-position.

CITATION LIST

Patent Literature

PTL 1: JP2003-183303A
PTL 2: JP2003-221339A
PTL 3: JP2003-221307A
PTL 4: WO2014/114723
NPL-1: CMC Publishing Co., Ltd., "*Wood Chemicals no Gijyutsu* (Techniques of Wood Chemicals)," First Edition 2007, p. 108

SUMMARY OF INVENTION

Technical Problem

When an acidic xylooligosaccharide is to be produced, increasing the production process efficiency and promoting cost reduction is one of the important issues. Further, when an acidic xylooligosaccharide is to be used as an intermediate for producing an active pharmaceutical ingredient, the acidic xylooligosaccharide is desirably usable as an intermediate (raw material) for producing an active pharmaceutical ingredient with a high yield.

An object of the present invention is to provide a method for producing an acidic xylooligosaccharide at a reduced cost. Another object of the present invention is to provide an acidic xylooligosaccharide for obtaining an active pharmaceutical ingredient with a high yield.

Means for Solving the Problem

As a result of extensive studies to solve the above problem, the present inventors have found that when a method for producing an acidic xylooligosaccharide includes a step of depolymerizing a plant-derived raw material, the production cost can be reduced. The inventors further found that when the method includes a deacetylation step, an acidic xylooligosaccharide with a reduced acetyl group content can be obtained, and that this acidic xylooligosaccharide can be used as a starting material for producing an active pharmaceutical ingredient with a high yield.

Specifically, the present invention has the following constitution.

[1] A method for producing an acidic xylooligosaccharide, comprising
 a depolymerization step of depolymerizing a plant-derived raw material; and
 a deacetylation step of adding a base to a solution of the product of the depolymerization step to achieve a pH of 11 or higher.
[2] The method for producing an acidic xylooligosaccharide according to [1], wherein the depolymerization step is at least one selected from a heat treatment step and an enzyme treatment step.
[3] The method for producing an acidic xylooligosaccharide according to [1] or [2], wherein the depolymerization step is a heat treatment step.

[4] The method for producing an acidic xylooligosaccharide according to [3], wherein the heat treatment step is a step of heating to 120° C. or higher under non-alkaline conditions.
[5] The method for producing an acidic xylooligosaccharide according to any one of [1] to [4], wherein the plant-derived raw material is a wood-derived raw material.
[6] The method for producing an acidic xylooligosaccharide according to any one of [1] to [4], further comprising a separation and purification step performed after the depolymerization step.
[7] The method for producing an acidic xylooligosaccharide according to any one of [1] to [6], further comprising a powdering step performed after the deacetylation step.
[8] An acidic xylooligosaccharide having an acetyl group content of 0 to 5.0 mass %.
[9] An acidic xylooligosaccharide having an acetyl group content of 0 to 0.7 mass %.
[10] The acidic xylooligosaccharide according to [8] or [9], wherein the acidic xylooligosaccharide has an average degree of polymerization of less than 8.
[11] A method for producing pentosan polysulfate, comprising sulfating the acidic xylooligosaccharide of any one of [8] to [10].

Advantageous Effects of Invention

According to the present invention, a method for producing an acidic xylooligosaccharide at a reduced production cost is provided. The production method of the present invention can efficiently produce an acidic xylooligosaccharide. The present invention can reduce the production cost of acidic xylooligosaccharide, and can thus provide an acidic xylooligosaccharide that is less expensive than conventional xylooligosaccharides. Further, the present invention provides an acidic xylooligosaccharide with a reduced acetyl group content that can be used as a starting material for producing pentosan sulfate with a high yield.

DESCRIPTION OF EMBODIMENTS

Figure 1:
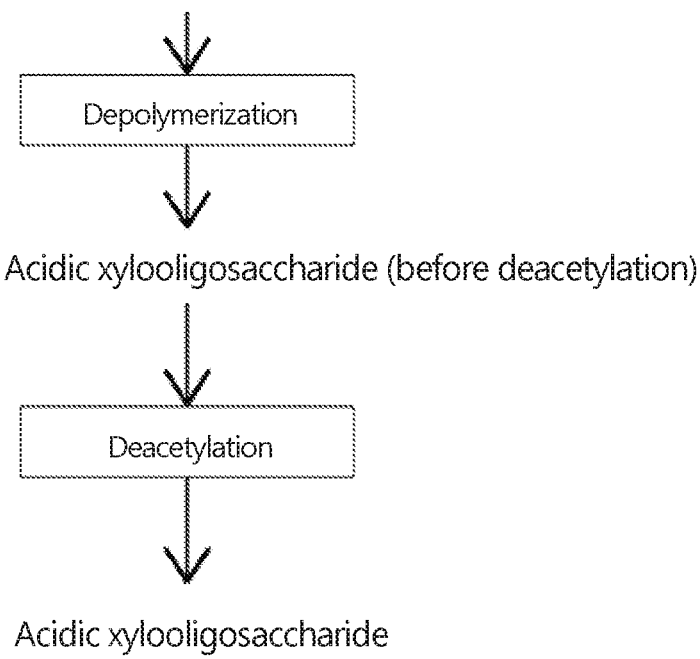
FIG. 1 is a schematic diagram showing a method for producing the acidic xylooligosaccharide of the present invention.

The present invention is described below in detail. The constituent features may be described below based on typical embodiments and specific examples; however, the present invention is not limited to these embodiments.
Acidic Xylooligosaccharide
The acidic xylooligosaccharide contains at least one uronic acid bound to at least one of the xylose units in a xylooligosaccharide molecule. That is, the acidic xylooligosaccharide has, as a side chain, at least one uronic acid residue per xylooligosaccharide molecule. The average number of uronic acid residues per acidic xylooligosaccharide molecule is preferably 1 or more and 3 or less, more preferably 1 or more and 2 or less. The average number of uronic acid residues per xylooligosaccharide molecule can be measured by the carbazole-sulfuric acid method, or the colorimetric method using sodium tetraborate.
Based on the disclosure of WO2014/114723 and "*Wood Chemicals no Gijyutsu* (Techniques of Wood Chemicals)" (CMC Publishing Co., Ltd.) referred to above, it is assumed that known acidic xylooligosaccharides obtained from xylan include a certain amount of xylose units to which acetyl groups ($-COCH_3$), as well as uronic acid residue(s), bind. The acidic xylooligosaccharide of the present invention has a lower acetyl group content; in particular, the acidic xylooligosaccharide also has a lower content of acetyl groups bound to specific xylose units, as described above.

More specifically, the acidic xylooligosaccharide of the present invention has an acetyl group content of 0 to 5.0% by mass. The acidic xylooligosaccharide preferably has an acetyl group content of 0 to 2.5 mass %, more preferably 0 to 1.0 mass %, particularly preferably 0 to 0.7 mass %, and most preferably substantially 0 mass %. Since the acidic xylooligosaccharide of the present invention has a low acetyl group content, the use of the acidic xylooligosaccharide as a starting material for pentosan polysulfate described below provides pentosan polysulfate with a high yield.

The average degree of polymerization of the acidic xylooligosaccharide is not particularly limited; however, it may be 40 or less, and is preferably 30 or less. When the production method of the present invention is used, an acidic xylooligosaccharide with a desired average degree of polymerization can be efficiently obtained. For example, as described above, there is a demand for an acidic xylooligosaccharide having an average degree of polymerization of less than 8. The production method of the present invention is particularly preferable as a method for producing an acidic xylooligosaccharide having an average degree of polymerization of less than 8 (for example, 7 or less).

The average degree of polymerization of the acidic xylooligosaccharide is preferably 2 or more, more preferably 3 or more. The average degree of polymerization of the acidic xylooligosaccharide can be calculated by dividing the total sugar amount of the acidic xylooligosaccharide by the amount of reducing sugar.

In calculation of the total sugar amount, first, an acidic xylooligosaccharide solution is maintained at 50° C., and centrifuged at 15000 rpm for 15 minutes. The total sugar amount of the supernatant is then quantified by the phenol-sulfuric acid method ("*Kangento no Teiryo-Ho* (Method of Quantifying Reducing Sugar)"; published by Gakkai Shuppan Center). The calibration curve to be used in this quantification is produced using D-xylose (Wako Pure Chemical Industries, Ltd.). The amount of reducing sugar is quantified by the Somogyi-Nelson method ("*Kangento no Teiryo-Ho* (Method of Quantifying Reducing Sugar)"; published by Gakkai Shuppan Center). The calibration curve to be used in this quantification is also produced using D-xylose (Wako Pure Chemical Industries, Ltd.).

The weight average molecular weight (Mw) of the acidic xylooligosaccharide is not particularly limited; however, it may be, for example, 3000 or less, or 2000 or less. In this case, the lower limit of the weight average molecular weight (Mw) of the acidic xylooligosaccharide is preferably 400.

Further, the weight average molecular weight (Mw) of the acidic xylooligosaccharide may be more than 3000, may be 4000 or more, or may be 5000 or more.

The number average molecular weight (Mn) of the acidic xylooligosaccharide is not particularly limited; however, it may be, for example, 3000 or less, or 2000 or less. In this case, the lower limit of the number average molecular weight (Mn) of the acidic xylooligosaccharide is preferably 400. The number average molecular weight (Mn) of the acidic xylooligosaccharide may be 3000 or more, 4000 or more, or 5000 or more.

The weight average molecular weight (Mw) and the number average molecular weight (Mn) of the acidic xylooligosaccharide obtained by the production method of the present invention can be measured by GPC (gel permeation chromatography). As the GPC column, a YMC-Pack Diol-300 and YMC-Pack Diol-60 (both manufactured by YMC) connected to each other can be used. The GPC conditions can be, for example, the following conditions.
Eluent: 25 mM potassium dihydrogen phosphate/25 mM dipotassium hydrogen phosphate/50 mM potassium chloride
Flow rate: 0.7 mL/min
Measurement temperature: 40° C.
Detector: refractive index detector
Analysis time: 40 minutes The degree of dispersion of the acidic xylooligosaccharide of the present invention is preferably 1.0 or more and 1.8 or less, and more preferably 1.0 or more and 1.6 or less. It is also preferable that the degree of dispersion of pentosan polysulfate is 1.0 or more and 1.4 or less. The degree of dispersion (D) of the acidic xylooligosaccharide is calculated by the following formula.

$$\text{Degree of dispersion}(D) = \text{Weight average molecular weight (Mw)/Number average molecular weight (Mn)}$$

Applications of Acidic Xylooligosaccharide

In particular, the acidic xylooligosaccharide obtained by the production method described below has high purity and tends to have a narrow molecular weight distribution. Therefore, the acidic xylooligosaccharide of the present invention can be preferably used for applications to foods, cosmetics, pharmaceuticals, etc. For example, compositions containing the acidic xylooligosaccharide can be provided as foods, cosmetics, and pharmaceuticals.

The acidic xylooligosaccharide obtained by the production method of the present invention can also be preferably used as an intermediate for producing an active pharmaceutical ingredient. In particular, the acidic xylooligosaccharide of the present invention is preferably used as a raw material for producing pentosan polysulfate with a high yield.

The production method of the present invention can control the average degree of polymerization of acidic xylooligosaccharide. Therefore, when the method of the present invention is performed and the obtained acidic xylooligosaccharide is subsequently sulfated, pentosan polysulfate having an average degree of polymerization and weight average molecular weight within the controlled ranges can be obtained.

Sulfation increases the molecular weight of acidic xylooligosaccharide about 2.5-fold. Therefore, for example, in order to obtain pentosan polysulfate having a weight average molecular weight (Mw) of 4000 or less, an acidic xylooligosaccharide with a weight average molecular weight (Mw) of 1600 or less (average degree of polymerization: about 10 or less) can be used. In order to obtain pentosan polysulfate having a weight average molecular weight (Mw) of 2400 or less, an acidic xylooligosaccharide with a weight average molecular weight (Mw) of 960 or less (average degree of polymerization: about 6 or less) can be used. Further, for example, in order to obtain pentosan polysulfate having a weight average molecular weight (Mw) of more than 4000, an acidic xylooligosaccharide with a weight average molecular weight (Mw) of more than 1600 (average degree of polymerization: more than about 10) can be used.

Method for Producing Acidic Xylooligosaccharide

The method for producing the acidic xylooligosaccharide of the present invention includes a step of depolymerizing a plant-derived raw material and a deacetylation step. As shown in FIG. 1, the method for producing the acidic xylooligosaccharide of the present invention may be any method that comprises a step of depolymerizing a plant-derived raw material and a deacetylation step in this order. The plant-derived raw material and the steps in the method for producing the acidic xylooligosaccharide of the present invention are described below.

Plant-Derived Raw Material

Examples of plant-derived raw materials include wood-derived raw materials, seed-derived raw materials, grain-derived raw materials, fruit-derived raw materials, and the like. Examples of plant-derived raw materials further include cottons such as cotton linter and cotton lint; herbaceous plants such as kenaf, hemp, ramie, and rice straw; and the like. Such raw materials derived from various sources may be used in combination as the plant-derived raw material.

Among these, wood-derived raw materials are particularly preferable as the plant-derived raw material. Examples of wood-derived raw materials include wood materials such as softwoods and hardwoods. The wood-derived raw material is preferably at least one selected from softwoods and hardwoods; and hardwoods are more preferable. The wood-derived raw material may be a mixture of softwood and hardwood. A bark may also be used as the wood-derived raw material.

Examples of hardwoods include beech, *Eucalyptus globulus, Eucalyptus grandis, Eucalyptus urograndis, Eucalyptus pellita, Eucalyptus braciana, Acacia mearnsii*, and the like. Examples of softwoods include Japanese cedar, Japanese cypress, pine, hiba, Japanese hemlock, and the like.

The wood-derived raw material preferably has a volume weight of 450 kg/m$^3$ or more and 700 kg/m$^3$ or less, and more preferably 500 kg/m$^3$ or more and 650 kg/m$^3$ or less. When the wood-derived raw material has a volume weight within the above-mentioned range, the efficiency of producing an acidic xylooligosaccharide can be enhanced.

The wood-derived raw material is preferably wood chips obtained by crushing one or more of the above-mentioned woods. When wood chips are used as a plant-derived raw material, depolymerization of the plant-derived raw material can efficiently proceed and the efficiency of producing acidic xylooligosaccharide can be enhanced.

Depolymerization Step

The method for producing the acidic xylooligosaccharide of the present invention comprises a step of depolymerizing a plant-derived raw material. Since the method includes the step of depolymerizing a plant-derived raw material, acidic xylooligosaccharide can be efficiently produced. This reduces the cost of producing the acidic xylooligosaccharide, and can thus provide a less-expensive acidic xylooligosaccharide.

The step of depolymerizing a plant-derived raw material is a step of chemically and/or physically decomposing a plant-derived raw material to produce an acidic xylooligosaccharide. Examples of the chemical and/or physical decomposition step include a heat treatment step, an alkali treatment step, an acid treatment step, an enzyme treatment step, an ionic liquid treatment step, a catalytic treatment step, and the like. Among these steps, the depolymerization step is preferably at least one selected from a heat treatment step and an enzyme treatment step; and is more preferably a heat treatment step. The heat treatment step may be a heating and pressurizing step. The depolymerization step is preferably performed under non-alkaline conditions (herein referred to as pH 9 or less, preferably pH 8 or less, and more preferably pH 7 or less).

The heat treatment step is a step of heating a plant-derived raw material in the presence of a solution. Since the plant-derived raw material is hydrolyzed in such a heat treatment step, the heat treatment step is sometimes referred to as a hydrolysis treatment step or a pre-hydrolysis treatment step. The solution used in the heat treatment step is preferably water. The ratio (mass ratio) of water to the plant-derived raw material is preferably in the range of 1:1 to 1:10. When the ratio of water to the plant-derived raw material is set within the above range, the hydrolysis reaction can proceed more efficiently. The water used in the heat treatment step may be water added separately from the plant-derived raw material; or a part of the water used in the heat treatment step may be water originally contained in the plant-derived raw material.

In the heat treatment step, in addition to the plant-derived raw material and water, other chemicals may also be added. Examples of such other chemicals include alkalis, acids, and chelating agents. Chemicals that directly or indirectly assist the depolymerization of polysaccharides, such as scale inhibitors, pitch control agents, and ionic liquid, may also be added.

The heat treatment step is a step of heating a plant-derived raw material in the presence of water. The heating temperature (liquid temperature) in this step is preferably 30° C. or higher, more preferably 50° C. or higher, even more preferably 75° C. or higher, still even more preferably 90° C. or higher, particularly preferably 100° C. or higher, and most preferably 120° C. or higher. On the other hand, the heating temperature (liquid temperature) is preferably 300° C. or lower, more preferably 250° C. or lower, and even more preferably 200° C. or lower.

The treatment time in the heat treatment step can be determined, as appropriate, according to the treatment temperature. The treatment time is, for example, preferably 5 minutes or more, more preferably 10 minutes or more, and even more preferably 20 minutes or more. The P factor expressed by the following formula is a product of temperature and time in the heating treatment. It is preferable to adjust the P factor within a preferred range.

$$P = \int_{t_0}^{t} \frac{k_{H1(T)}}{k_{100°C.}} \cdot dt = \int_{t_0}^{t} \mathrm{Exp} \cdot \left(40.48 - \frac{15106}{T}\right) \cdot dt$$

In the above formula, P represents P factor, T represents absolute temperature (Celsius temperature (° C.)+273.5), t represents heat treatment time, and $K_{H1(T)}/K_{100° C.}$ represents the relative rate of hydrolysis of glycosidic bonds.

In the heat treatment step, the P factor is preferably set at 200 or more, more preferably 250 or more, and even more preferably 300 or more. On the other hand, the P factor is preferably 1000 or less. In the heat treatment step, the P factor is adjusted as appropriate so that the average degree of polymerization of acidic xylooligosaccharide is within a desired range, whereby the molecular weight of the obtained pentosan polysulfate can be adjusted. Furthermore, the energy efficiency of the hydrolysis reaction can be increased.

For example, an acidic xylooligosaccharide having an average degree of polymerization of less than about 8 can be obtained by performing a heat treatment step at an absolute temperature for a heat treatment time such as to achieve a P factor of 800 or more and 1000 or less. Further, an acidic xylooligosaccharide having a weight average molecular weight of about 1800 (the average degree of polymerization: about 12) to about 5000 (the average degree of polymerization: about 33) can be obtained by performing a heat treatment step at an absolute temperature for a heat treatment time such as to achieve a P factor of 100 or more and 400 or less. Further, an acidic xylooligosaccharide having a weight average molecular weight of more than 1200 (the average degree of polymerization: about 8) and less than about 1800 (the average degree of polymerization: about 12) can be obtained by performing a heat treatment step at an absolute temperature for a heat treatment time such as to achieve a P factor of less than 800 and more than 400.

In the heat treatment step, the solution containing a plant-derived raw material preferably has a pH of 9 or less, more preferably a pH of 8 or less, and even more preferably a pH of 7 or less. That is, the heat treatment step is preferably performed under non-alkaline conditions. The pH value described above refers to the pH of the solution before the heat treatment.

In the heat treatment step, a raw material-derived acid may be dissociated, and acid hydrolysis may proceed at least partially. Examples of plant raw material-derived acids include organic acids, such as acetic acid and formic acid. In this case, the solution containing a plant-derived raw material has a further reduced pH after the acid hydrolysis.

In the production method of the present invention, the depolymerization step is preferably a heat treatment step. This can increase the efficiency of producing acidic xylooligosaccharide. The heat treatment step can significantly reduce the number of steps required to produce acidic xylooligosaccharide, as compared with the conventional methods. When the heat treatment is performed under non-alkaline conditions, acidic xylooligosaccharide can be efficiently produced with suppressed coloration, because the acidic xylooligosaccharide is not substituted with hexenuronic acid.

In the present invention, the depolymerization step is preferably a heat treatment step; however, it can be a step other than the heat treatment step. For example, when the depolymerization step is an enzyme treatment step, the depolymerization step comprises a step of mixing a plant-derived raw material with an enzyme. Examples of usable enzymes include hemicellulase and the like. Specific examples include commercially available enzyme preparations, such as Cellulosin HC100 (trade name, manufactured by HBI Enzymes Inc.), Cellulosin TP25 (trade name, manufactured by HBI Enzymes Inc.), Cellulosin HC (trade name, manufactured by HBI Enzymes Inc.), Cartazyme (trade name, manufactured by Clariant AG), Ecopulp (trade name, manufactured by Rohm Enzyme GmbH), Sumizyme (trade name, manufactured by Shin Nihon Chemicals Corporation), Pulpzyme (manufactured by Novo Nordisk), and Multifect 720 (Genencor); and xylanase produced by microorganisms belonging to genus *Trichoderma*, genus *Thermomyces*, genus *Aureobasidium*, genus *Streptomyces*, genus *Aspergillus*, genus *Clostridium*, genus *Bacillus*, genus *Thermotoga*, genus *Thermoascus*, genus *Cardoceram*, genus *Thermomonospora*, or the like.

In the enzymatic treatment step, an enzyme is added to a solution obtained by mixing a plant-derived raw material with water. The temperature of the solution during this addition is preferably 10° C. or higher and 90° C. or lower, and more preferably 30° C. or higher and 60° C. or lower. The temperature of the solution is preferably a temperature close to the optimal temperature of the enzyme used. The pH of the solution is also preferably adjusted to a range in which the activity of the enzyme is enhanced. For example, the pH of the solution is preferably adjusted to a pH of 3 or more and 10 or less.

When the depolymerization step is an alkali treatment step or an acid treatment step, the depolymerization step comprises a step of mixing a plant-derived raw material with an alkaline solution or an acid solution. In the alkali treatment step, sodium hydroxide or potassium hydroxide is preferably added. In the acid treatment step, hydrochloric acid, sulfuric acid, acetic acid, or the like is preferably added. In this case as well, heating or pressurization may be performed as appropriate.

When the depolymerization step is at least one selected from an enzyme treatment step, an alkali treatment step, and an acid treatment step, the production method may further comprise, after the treatment step, a squeezing step, an extraction step, a heating step, a filtration step, a separation step, a purification step, a concentration step, a desalting step, or the like. The method may further comprise a molecular weight reduction step after the treatment step. Examples of other steps include the steps described in JP2003-183303A, the contents of which are incorporated herein by reference.

Filtration Step

After completion of the depolymerization step described above, the reaction mixture is separated into solids of the plant-derived raw material, and a solution other than the solids. More specifically, when the method comprises a filtration step that is performed after the depolymerization step, the reaction product is separated into solids, which are used as a pulp raw material, and a filtrate. The solids used as a pulp raw material are subjected to a digestion step or the like as a post-step to thereby provide a cellulose raw material (dissolving pulp).

The collected filtrate can be separated into a gas layer and a liquid layer. Since the gas layer contains a large amount of furfurals, furfurals can be isolated by collecting these furfurals from the gas layer. On the other hand, the liquid layer contains a large amount of hemicellulose comprising acidic xylooligosaccharide and neutral xylooligosaccharide. The acidic xylooligosaccharide contained in this liquid layer can be separated and purified in the step described below.

Separation and Purification Step

Figure 2:
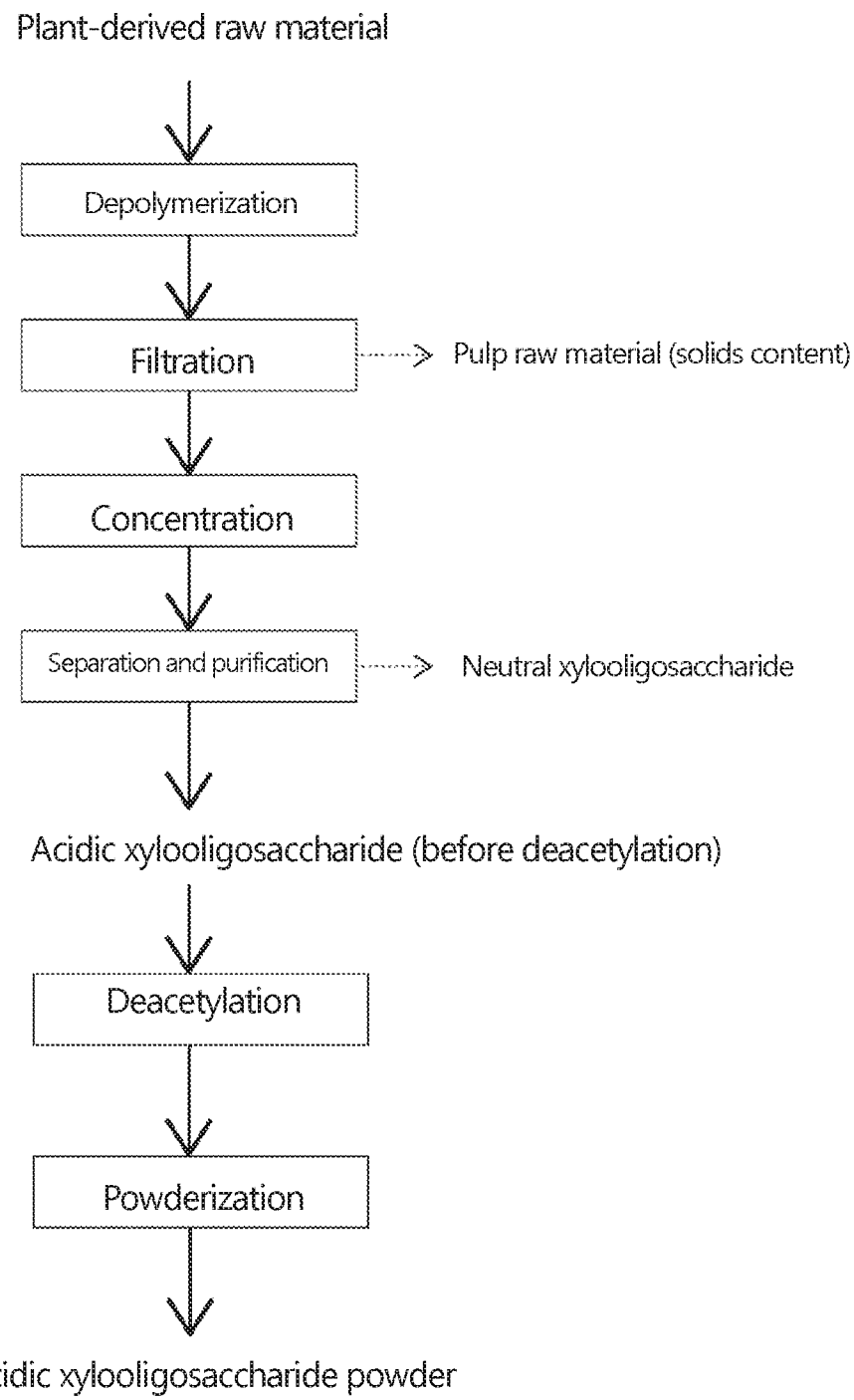
FIG. 2 illustrates an example of a method for producing the acidic xylooligosaccharide.

The method for producing the acidic xylooligosaccharide of the present invention preferably further comprises a separation and purification step after the depolymerization step. The separation and purification step may be provided immediately after the depolymerization step. However, it is preferable that a filtration step is provided after the depolymerization step, and a separation and purification step is provided after the filtration step, so that the acidic xylooligosaccharide is separated from the obtained filtrate and purified. The filtration step may be provided as a part of the separation and purification step; or, as shown in FIG. 2, the filtration step may be provided between the depolymerization step and the separation and purification step. The separation and purification step is a step of separating and purifying the acidic xylooligosaccharide. Since the filtrate obtained in the filtration step contains various saccharides, such as neutral xylooligosaccharide, in addition to acidic xylooligosaccharide, the separation and purification step is also a step of removing such xylooligosaccharides other than the acidic xylooligosaccharide.

In the separation and purification step, for example, ion exchange chromatography, affinity chromatography, gel filtration, ion exchange treatment, NF membrane treatment, UF membrane treatment, RO membrane treatment, activated carbon treatment, or like methods are preferably used. In the separation and purification step, it is also preferable to perform the above methods in combination. In particular, when ion exchange chromatography is performed in the separation and purification step, acidic xylooligosaccharide can be selectively separated and purified. In ion exchange chromatography, acidic xylooligosaccharide is adsorbed to thereby mainly obtain acidic xylooligosaccharide from the sugar liquid (filtrate). Specifically, sugar liquid is first treated with a strong cation exchange resin to remove metal ions from the sugar liquid. Subsequently, using a strong anion exchange resin, sulfate ions or the like are removed from the sugar liquid. The resulting sugar liquid is treated with a weak anion exchange resin to adsorb acidic xylooligosaccharide on the resin. The acidic oligosaccharide adsorbed on the resin is eluted with a low-concentration salt ($NaCl$, $CaCl_2$, $KCl$, $MgCl_2$, etc.) to thereby obtain an acidic xylooligosaccharide solution containing a small amount of impurities.

Concentration Step

As shown in FIG. 2, the method for producing the acidic xylooligosaccharide of the present invention preferably comprises a concentration step between the depolymerization step and the separation and purification step. The concentration step is more preferably provided after the filtration step, which is provided after the depolymerization step, and before the separation and purification step. When the method includes this concentration step, the subsequent separation and purification step can be more efficiently performed, and the efficiency of producing an acidic xylooligosaccharide can be increased.

Examples of the concentration step include a membrane treatment step using an NF membrane, an ultrafiltration membrane, a reverse osmosis membrane, or the like; a concentration step using evaporation etc.; and the like.

In the concentration step, the solution is preferably concentrated, so that the resulting concentrate has an acidic xylooligosaccharide content of 10% or more and 80% or less, and more preferably 20% or more and 60% or less, based on the total mass of the concentrate.

Deacetylation Step

The method for producing acidic xylooligosaccharide of the present invention comprises a deacetylation step. The deacetylation step may be included at any stage after the depolymerization step. The production method of the present invention, which comprises a deacetylation step, can obtain an acidic xylooligosaccharide with a low acetyl group content.

The deacetylation step is a step of adding a base to achieve a pH of 11 or more. More specifically, the deacetylation step is a step of adding a base to adjust the pH of a solution containing a substance obtained from a plant-derived raw material, such as acidic xylooligosaccharide (herein also referred to as a "solution containing acidic xylooligosaccharide or the like") to pH 11 or more. In the deacetylation step, the solution obtained after the depolymerization; the filtrate obtained in the filtration step; or the solution containing acidic xylooligosaccharide after the separation and purification step may be adjusted to a pH of 11 or higher. That is, a base may be added to a solution containing a product obtained through the depolymerization step (acidic xylooligosaccharide before deacetylation) so as to achieve a pH of 11 or more. The solution containing acidic xylooligosaccharide may also be herein referred to as an acidic xylooligosaccharide solution. The solution is preferably an aqueous solution.

The pH applied in the deacetylation step is preferably pH 11 to 14, and more preferably pH 12 to 13. The solution containing acidic xylooligosaccharide is preferably maintained at pH 11 or higher for 0.5 hours or more, more preferably at pH 11 or higher for 1.0 hour or more, even more preferably at pH 11 or higher for 2.0 hours or more, and particularly preferably at pH 11 or higher for 3.0 hours or more. In particular, when the pH is lower than 12, the solution is preferably maintained for 1.0 hour or more. Particularly preferred conditions can be, for example, conditions in which solution is maintained at pH 12 to 13 for 3 hours or more.

While the solution is maintained in the pH range described above, the solution is preferably stirred. The temperature conditions while the solution is maintained in the pH range are not particularly limited; however, the temperature is preferably room temperature.

The base to be added in the deacetylation step is not particularly limited, as long as the desired pH can be achieved. The base is preferably sodium hydroxide.

The deacetylation step may comprise a pH adjustment step of adjusting, to less than pH 11, an acidic xylooligosaccharide-containing solution having pH 11 or more due to a base added after the solution is maintained at the pH described above. In the pH adjustment step, the solution may be adjusted to, for example, pH 9 or less, pH 8 or less, pH 7 or less, pH 6 or less, pH 5 or less, pH 4 or less, or the like. The adjustment may be performed by adding an acid. Examples of acids include hydrochloric acid.

The deacetylation step may also preferably comprise a desalting step after the pH adjustment step. Desalting can be performed, for example, using a dialysis membrane or an NF membrane.

The deacetylation step may further comprise a step of powdering the obtained product for the subsequent treatment.

Dehydration Step

In the production method of the present invention, the acidic xylooligosaccharide may be obtained in the form of an acidic xylooligosaccharide solution; or may be subjected to a dehydration step, and thereby obtained in the form of an acidic xylooligosaccharide concentrate, or in the form of an acidic xylooligosaccharide powder. When an acidic xylooligosaccharide powder is to be produced, the production method preferably further comprises a powdering step after the deacetylation step, as shown in FIG. 2.

In the powdering step, the acidic xylooligosaccharide solution obtained in the deacetylation step is treated, for example, using a spray dryer, a freeze-drying machine, a hot-air drying machine, or a water-soluble organic solvent, to thereby obtain an acidic xylooligosaccharide powder.

EXAMPLES

The features of the present invention are described below more specifically with reference to Examples. The materials, amounts used, proportions, treatment content, treatment procedures, and the like described in the following Examples can be appropriately changed as long as such changes do not depart from the spirit of the present invention. Accordingly, the scope of the present invention should not be construed as being limited by the following specific examples.

Reference Example

Production of Acidic Xylooligosaccharide

Forty parts by mass of water was added to 10 parts by mass of wood chips (hardwood), and a heat treatment was performed at 160° C. for 3 hours. The resulting mixture was then subjected to solid-liquid separation using a Screw Press (manufactured by Shinryo Seisakusho: 250×1000 SPH-EN), and the filtrate was recovered. The filtrate was further filtered through a bag filter with a micron rate of 1 μm (manufactured by ISP Filters). After 5 parts by mass of activated carbon (PM-SX; manufactured by Mikura Kasei Kabushiki Kaisha) was added to treat the filtrate at 50° C. for 2 hours, the treatment mixture, including the activated carbon, was further filtered through a ceramic filter with a micron rate of 0.2 μm (manufactured by Nihon Pall Co., Ltd.) to recover a clear filtrate. After the clear filtrate was concentrated 20-fold with a reverse osmosis membrane (NTR-7450; manufactured by Nitto Denko Corporation) to obtain a concentrated sugar liquid, the concentrated sugar liquid was passed at SV 1.5 through a 4-bed 4-tower type ion exchange resin system consisting of a strong cationic resin (PK-218; manufactured by Mitsubishi Chemical Corporation), a weak anionic resin (WA30; manufactured by Mitsubishi Chemical Corporation), a strong cationic resin (PK-218; manufactured by Mitsubishi Chemical Corporation), and a weak anionic resin (WA30; manufactured by Mitsubishi Chemical Corporation). Acidic xylooligosaccharide was adsorbed on the weak anionic resin of the second and fourth towers. A 50 mM sodium chloride aqueous solution was then passed through the second and fourth towers at SV 1.5 to recover an acidic xylooligosaccharide solution. Thereafter, the obtained acidic xylooligosaccharide solution was powdered using a spray dryer (manufactured by Okawara Kogyo Co., Ltd.).

Average Degree of Polymerization of Acidic Xylooligosaccharide

A sample sugar liquid was prepared by adding 1000 parts by mass of water to 1 part by mass of the powdered acidic xylooligosaccharide. This sample sugar liquid was maintained at 50° C. and filtered through a 0.45 μm filter to obtain the total sugar amount. The total sugar amount in the filtrate was divided by the amount of reducing sugar (both in terms of xylose) to obtain an average degree of polymerization.

The total sugar amount was quantified by the phenol-sulfuric acid method ("*Kangento no Teiryo-Ho* (Method of Quantifying Reducing Sugar)"; published by Gakkai Shuppan Center) using a calibration curve prepared using D-xylose (Wako Pure Chemical Industries, Ltd.). The amount of reducing sugar was quantified by the Somogyi-Nelson method ("Quantitative Method for Reducing Sugar" published by Gakkai Shuppan Center) using a calibration curve prepared using D-xylose (Wako Pure Chemical Industries, Ltd.).

The average degree of polymerization of the acidic xylooligosaccharide was 6.

As described above, an acidic xylooligosaccharide having an average degree of polymerization of less than 8 was obtained. The production method consisted of a smaller number of steps, could be performed very easily, and makes it possible to produce an acidic xylooligosaccharide at a significantly reduced cost.

Example 1

Production of Acidic Xylooligosaccharide

In order to achieve the pH shown in the table below, sodium hydroxide was added to a solution of the acidic xylooligosaccharide with an average degree of polymerization of 6 (before deacetylation), which was obtained by passing the liquid through the column in the same manner as in the Reference Example; and the resulting mixture was stirred for the time shown in the table below for deacetylation. Hydrochloric acid was added to the obtained solution to achieve a pH of less than 5. Desalting was performed using a dialysis membrane (Spectra/Por, manufactured by Spectrum Chemical Manufacturing Corp.). The obtained acidic xylooligosaccharide solution was powdered using a freeze-drying machine (manufactured by Eyela).

Production of Pentosan Polysulfate Sodium 10 mL of N,N-dimethylformamide, 2.4 g of sulfur trioxide pyridine complex, and 0.3 g of the acidic xylooligosaccharide powder produced by the above-described method were added to a 100 mL separable flask, and allowed to react at 40° C. for 3 hours. After cooling, the obtained reaction mixture was added dropwise to 500 mL of ethanol. The generated precipitate was collected by filtration, and 30 mL of water was added to dissolve the precipitate therein. A sodium hydroxide solution was added to this solution to achieve a pH of 10. The resulting solution was added dropwise to 500 mL of ethanol, and the obtained precipitate was collected by filtration. Thereafter, 50 mL of water was added to dissolve the precipitate therein. After activated carbon was added to the solution and stirred, the resulting mixture was filtered. The filtrate was concentrated using an evaporator, and powdered using a freeze-drying machine (manufactured by Eyela).

Weight Average Molecular Weight

The weight average molecular weight (Mw) and the number average molecular weight (Mn) of pentosan polysulfate sodium shown in Table 1 were measured by GPC (gel permeation chromatography). As the GPC column, a YMC-Pack Diol-300 and YMC-Pack Diol-60 (both manufactured by YMC) connected to each other were used. GPC was performed under the following conditions.

Eluent: 25 mM potassium dihydrogen phosphate/25 mM dipotassium hydrogen phosphate/50 mM potassium chloride
Flow rate: 0.7 mL/min
Measurement temperature: 40° C.
Detector: refractive index detector
Analysis time: 40 minutes Sulfur Content The sulfur content of pentosan polysulfate sodium was measured by the oxygen flask combustion method described in the Japanese Pharmacopoeia.

Measurement of Anti-Xa Activity

The anti-Xa activity of pentosan polysulfate sodium was measured using Test Team (registered trademark) Heparin S (manufactured by Sekisui Medical Co., Ltd.).

Measurement of Anti-IIa Activity

The anti-IIa activity of pentosan polysulfate sodium was measured using Biophen heparin anti-IIa (manufactured by Hyphen BioMed).

TABLE 1

|  | Comparative Example 1 | Example 1 | Example 2 | Example 3 | Example 4 | Example 5 |
| --- | --- | --- | --- | --- | --- | --- |
| Deacetylation conditions | No treatment | pH 11 1 hr | pH 11 2 hr | pH 12 0.5 hr | pH 12 1 hr | pH 13 3 hr |
| Weight average molecular weight | 2211 | 2356 | 2325 | 2178 | 2129 | 2155 |
| Acetyl group content of pentosan polysulfate sodium (mass %) | 2.793 | 1.618 | 0.866 | 0.470 | 0.217 | 0.000 |
| Acetyl group content of acidic xylooliclosaccharide (mass %) | 6.983 | 4.405 | 2.165 | 1.175 | 0.543 | 0.000 |
| Sulfur content (mass %) | 16.27 | 14.33 | 15.12 | 15.09 | 15.34 | 15.28 |
| FIIa activity (IU/mg) | 0.0221 | 0.1405 | 0.1845 | 0.0676 | 0.0934 | 0.0976 |
| FXa activity (IU/mg) | 0.0840 | 0.2047 | 0.2588 | 0.2439 | 0.2419 | 0.2297 |
| EXa/FIIa ratio | 3.801 | 1.457 | 1.403 | 3.607 | 2.591 | 2.352 |

Acetyl Group Content 35 mg of sodium 3-(trimethylsilyl)propionate-2,2,3,3-d4 (Isotec Corporation) was dissolved in heavy water (Kanto Kagaku). Using a 25-mL measuring flask, the solution was diluted to prepare an internal standard solution. The pentosan polysulfate sodium obtained in each of the Examples and Comparative Examples was weighed (30 mg) and dissolved in 1 mL of the internal standard solution to prepare a solution for NMR analysis. The obtained solution was transferred to an NMR sample tube (Kanto Kagaku), and $^1$H-NMR measurement was performed using FT-NMR (JNM-LA400; JEOL Ltd.). The acetyl group content was calculated from the integral ratio of the acetyl peak of pentosan polysulfate sodium to the trimethylsilyl peak of the internal standard substance.

The acetyl group content of the acidic xylooligosaccharide as a starting material was calculated by multiplying the obtained acetyl group content of pentosan polysulfate sodium by 2.5.

The yields of pentosan polysulfate sodium powder obtained from the acidic xylooligosaccharide powder under the conditions of Comparative Example 1 and Example 5 were confirmed. Table 2 shows the results.

TABLE 2

| Comparative Example 1 | Exmple 5 |
| --- | --- |
| About 18.1% (yield: 0.1391 g, amount added: 0.3072 g) | About 40.9% (yield: 0.3181 g, amount added: 0.3108 g) |

The results of Tables 1 and 2 show that when an acidic xylooligosaccharide having a reduced acetyl group content is used, pentosan polysulfate sodium that can be used for pharmaceutical applications can be obtained with a high yield.

The invention claimed is:

1. A method for producing an active pharmaceutical ingredient including pentosan polysulfate, comprising:
   (A) a step for producing an acidic xylooligosaccharide, the step comprising
      (i) depolymerizing a plant-derived raw material;
      (ii) adding a base to a solution of the product of the depolymerization step (i) to achieve a pH of 11 or higher; and
      (iii) obtaining an acidic xylooligosaccharide having an acetyl group content of 0 to 0.7 mass %; and
   (B) a step for producing the active pharmaceutical ingredient, the step comprising sulfating the acidic xylooligosaccharide.

2. The method according to claim 1, wherein the depolymerization step (i) comprises at least one step selected from the group consisting of a heat treatment step and an enzyme treatment step.

3. The method according to claim 1, wherein the depolymerization step (i) is a heat treatment step.

4. The method according to claim 3, wherein the heat treatment step is a step of heating to 120° C. or higher under non-alkaline conditions.

5. The method according to claim 1, wherein the plant-derived raw material is a wood-derived raw material.

6. The method according to claim 1, further comprising a separation and purification step performed after the depolymerization step (i).

7. The method according to claim 1, further comprising a powdering step performed after the step (ii).

* * * * *

UNITED STATES PATENT AND TRADEMARK OFFICE
CERTIFICATE OF CORRECTION

Page 1 of 1

PATENT NO. : 11,286,272 B2
APPLICATION NO. : 16/643215
DATED : March 29, 2022
INVENTOR(S) : Kotaro Ishikawa et al.

It is certified that error appears in the above-identified patent and that said Letters Patent is hereby corrected as shown below:

On the Title Page

Under (30) Foreign Application Priority Data
Delete "Aug. 31, 2016 (JP) ......................... 2016-169709" and insert --NONE-- therefor.

Signed and Sealed this
Second Day of August, 2022

Katherine Kelly Vidal
*Director of the United States Patent and Trademark Office*